United States Patent [19]

Lawson

[11] Patent Number: 5,219,481

[45] Date of Patent: Jun. 15, 1993

[54] OXIME COMPOUND, PREPARATION AND USE FOR COATING AND LUBRICATING METALS

[75] Inventor: John R. Lawson, Manchester, England

[73] Assignee: Imperial Chemical Industries PLC, London, England

[21] Appl. No.: 868,234

[22] Filed: Apr. 14, 1992

[30] Foreign Application Priority Data

Apr. 18, 1991 [GB] United Kingdom ............... 9108221

[51] Int. Cl.$^5$ ............... C10L 133/30; C07C 251/36; B21B 45/02
[52] U.S. Cl. ............... 252/51.5 R; 252/51; 252/54; 252/58; 106/14.15; 106/14.37; 564/265; 564/266; 72/41
[58] Field of Search ............... 564/265, 266, 259; 252/51, 51.5 R; 106/14.15, 14.37

[56] References Cited

U.S. PATENT DOCUMENTS

| | | | |
|---|---|---|---|
| 1,921,424 | 8/1933 | Nabenhauer | 564/259 |
| 2,562,205 | 7/1951 | Novotny et al. | 564/259 |
| 4,133,834 | 1/1979 | Pickens | 564/259 |
| 4,493,876 | 1/1985 | Birkett et al. | 106/14.15 |
| 4,613,384 | 9/1986 | John | 106/14.15 |
| 4,697,038 | 9/1987 | Tyman | 564/265 |
| 5,041,666 | 8/1991 | Ward et al. | 564/265 |

FOREIGN PATENT DOCUMENTS

| | | |
|---|---|---|
| 125025 | 11/1984 | European Pat. Off. . |
| 178850 | 4/1986 | European Pat. Off. . |
| 1365291 | 8/1974 | United Kingdom . |
| 1372522 | 10/1974 | United Kingdom . |
| 1421766 | 1/1976 | United Kingdom . |
| 1563206 | 3/1980 | United Kingdom . |
| 2222592 | 3/1990 | United Kingdom . |

*Primary Examiner*—Prince Willis, Jr.
*Assistant Examiner*—Alan D. Diamond
*Attorney, Agent, or Firm*—Cushman, Darby & Cushman

[57] ABSTRACT

A tetraoximino derivative of a bisphenol, for example the 3,5,3$^1$,5$^1$-tetraoximino methyl derivative of 2,2-bis(4-hydroxyphenyl) propane, can be coated onto a metal surface to give improved corrosion resistance. The metal surface can be zinc coated steel or zinc phosphated steel. The tetraoximino derivative can be the only coating material or can be incorporated into a surface coating composition such as paint.

8 Claims, No Drawings

OXIME COMPOUND, PREPARATION AND USE FOR COATING AND LUBRICATING METALS

The present invention relates to a new class of compound, the preparation and use thereof, particularly the use to improve the resistance of a metal to oxidative, and or other, deterioration.

Metals can be subject to deterioration by oxidation of the surface thereof. This oxidation may extend through the metal and can ultimately result in mechanical failure of the metal. The oxidation may also result in the failure of a bond between the metal and a surface coating such as a paint coating or may result in the failure of a bond between two metal surfaces. This oxidation is generally referred to as corrosion and more specifically with iron and steel as rust.

Various proposals have been made in an attempt to minimise corrosion of metal surfaces. One method is to coat the metal surface, for example by painting the surface. However, whilst the paint may reduce corrosion, the paint coating may be permeable to some extent to oxygen and/or water vapor, which are the main causes of corrosion. Furthermore, the paint coating may not adhere satisfactorily to the metal surface and may eventually peel off leaving the metal surface exposed to the environment and hence to corrosion.

An alternative procedure is to apply a protective coating to the metal, for example by a phosphate treatment. However, whilst a phosphate treatment gives some protection, the processing conditions need to be precisely controlled. Furthermore, subsequent to the phosphate treatment, it is necessary to rinse the metal and this is typically effected in two stages, the first stage being a water rinse and the second stage being with a passivating solution. A rinse with a solution containing a hexavalent chromium compound has been used but, in view of environmental considerations due to the toxicity of hexavalent chromium, the use of such chromium compounds requires the use of stages to minimise the release of hexavalent chromium into the environment. Reducing the quantities of hexavalent chromium compound in effluent requires treatment equipment and adds to the costs of using such materials.

In recent years, alternatives to the phosphate treatment and/or the use of hexavalent chromium compounds have been sought. In our European Patent No 125025 we disclose a process for the inhibition of the corrosion of metals which comprises treating the metal with an optionally substituted 2-hydroxy-5-alkylbenzaldoxime wherein the 5-alkyl substituent contains from 7 to 13 carbon atoms. In our European Patent No 178850 we disclose a process for the inhibition of the corrosion of metals which comprises treating the metal with an optionally substituted bis(oximinomethyl)alkylphenol having a specified formula. The preferred compounds used in the process of European Patent No 178850 are optionally substituted 2,6-bis(oximinomethyl)-4-alkylphenols such as 2,6-bis(oximinomethyl)-4-nonylphenol. The procedures of European Patents No 125025 and 178850 give good corrosion protection, particularly to iron-based substrates, but further improvements are desirable.

According to the present invention there is provided a compound of the general formula (I):

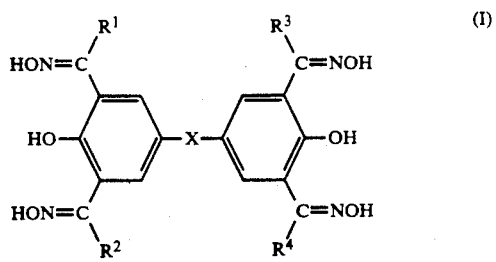

wherein $R^1$, $R^2$, $R^3$ and $R^4$ are each, independently, hydrogen, a hydrocarbon group or a substituted hydrocarbon group; and X is a direct bond or a divalent linking group.

Whilst the groups $R^1$, $R^2$, $R^3$ and $R^4$ may be different, compounds in which the groups $R^1$, $R^2$, $R^3$ and $R^4$ are the same are more readily prepared and are the preferred compounds. If one or more of the groups $R^1$, $R^2$, $R^3$ and $R^4$ is a substituted hydrocarbon group, the substituents may be hydrocarbonoxy, halogen, nitro or nitrile. Any hydrocarbon group which is present is preferably one which contains up to 20 carbon atoms. The hydrocarbon group may be an alkyl, cycloalkyl or aryl group or may be a combination of such groups as in alkaryl and aralkyl groups. If the hydrocarbon group is an alkyl group it preferably contains up to five carbon atoms and is especially methyl. Hydrocarbon groups which are, or which contain, an aryl group preferably contain from six up to fifteen carbon atoms, for example phenyl, benzyl and tolyl groups. Preferably all of the groups $R^1$, $R^2$, $R^3$ and $R^4$ are hydrogen atoms.

The group X may be a direct bond but is preferably a divalent linking group. Thus, the group X is preferably a divalent hydrocarbon or substituted hydrocarbon group or may be a divalent linking group such as a sulphoxide, sulphone, carbonyl or oxygen group. If the group X is a substituted hydrocarbon group, the substituents may be hydroxyl, halogen, nitro, nitrile, hydrocarbonoxy, hydrocarbonoxycarbonyl, acyl, amino, carboxylic acid, sulphonic acid, sulphonamide or similar substituent atoms or groups. There may be more than one substituent group present and these groups may be the same or different. If the group X is a substituted hydrocarbon group, this conveniently contains an aromatic ring to which the substituent or substituents are attached. If the group X is a hydrocarbon or substituted hydrocarbon group, this may be methylene; ethylene; ethylidene; propylene; propylidene; dimethylmethylene ($(CH_3)_2C=$); butylene; pentylene; phenylmethylene; methylphenylmethylene; methyl-4-substituted phenylmethylene and the like. The bonding to the group X when this is an optionally substituted hydrocarbon group may be to the same carbon atom, as in the methylene, ethylidene, propylidene, dimethylmethylene group and the like. Alternatively, the bonding may be to adjacent carbon atoms, as in the ethylene, propylene, butylene, pentylene group and the like. Alternatively, the bonding may be to different carbon atoms which are not adjacent such as the terminal carbon atoms of a hydrocarbon chain as in tri-, tetra, and penta-methylene group and the like. The group X may be any divalent linking group but is preferably a relatively simple linking group since these are generally more readily available.

Compounds of the general formula (I) in accordance with the present invention will be referred to as "tetraoximes", and include, inter alia, bis (4-hydroxy-3,5-dioximinomethyl phenyl) methane;
2,2-bis(4-hydroxy-3,5-dioximinomethyl phenyl)propane;
3,3-bis(4-hydroxy-3,5-dioximino methylphenyl)pentane;
2,2-bis(4-hydroxy-3,5-dioximinomethylphenyl)pentane and
1-phenyl-1,1-bis(4-hydroxy-3,5-dioximino methylphenyl)ethane.

The tetraoxime can be prepared from the corresponding aldehyde or ketone, which is a tetra-aldehyde or a tetra-ketone.

As a further aspect of the present invention there is provided a compound of the general formula (II).

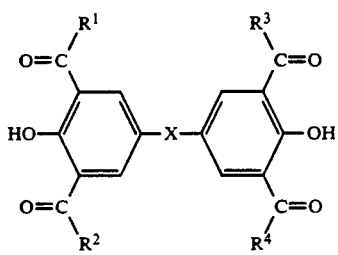

wherein
$R^1$, $R^2$, $R^3$, $R^4$ and X are as hereinbefore defined.

Preferably groups $R^1$, $R^2$, $R^3$ and $R^4$ are all hydrogen atoms and the compound of formula (II) is a tetra-aldehyde.

A compound of general formula (II) can be reacted with hydroxylamine or hydroxylamine salt to obtain an oxime, preferably a tetraoxime.

Thus, as a further aspect of the present invention, a compound of the general formula (II) is reacted with a sufficient quantity of a hydroxylamine or hydroxylamine salt to obtain a tetraoxime.

The reaction is preferably effected using hydroxylamine or hydroxylamine salt in an amount greater than the stoichiometric amount required to form a tetraoxime. The reaction is conveniently effected by adding a solution of hydroxylamine or hydroxylamine salt to the compound of the formula (II) conveniently suspended or dissolved, in a suitable liquid medium. The compound of formula (II) may be suspended in a liquid such as industrial methylated spirits, dichloromethane, chloroform, carbon tetrachloride, toluene, and alkanols particularly $C_1$–$C_6$ lower alkanols such as methanol, ethanol propanol and butanol.

The reaction is desirably effected at an elevated temperature which is typically at least 50° C. and may be as high as 120° C. and preferably is not more than 100° C., and conveniently is the reflux temperature of the mixture. The reaction is effected for a time which is typically at least 30 minutes and may be 10 hours or more but conveniently is at least one hour and not more than six hours.

The tetraoxime product may be recovered by filtration, washing and drying in the known manner. The purity of the final product is dependent on the quantity of hydroxylamine or hydroxylamine salt used and also on the purity of the compound of formula (II).

Compounds of formula (II) in which the groups $R^1$, $R^2$, $R^3$ and $R^4$ are all hydrogen can be prepared from the corresponding bis-phenol of formula (III).

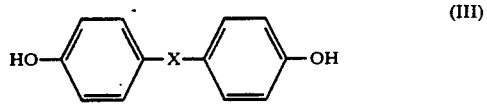

where X is as defined by reaction with hexamethylenetetramine and hydrolysis of the intermediate product.

The reaction with hexamethylenetetramine is preferably carried out under conditions to form a Schiff's base which is then hydrolysed by reaction with an aqueous acid. The proportion of hexamethylenetratramine used should be sufficient to form the desired tetra-aldehyde on hydrolysis. The reaction is effected at an elevated temperature which is typically at least 50° C., particularly at least 80° C. and especially at least 100° C. The reaction temperature should not be so high as to cause breakdown of the bis-phenol of formula (III) and hence preferably does not exceed 180° C. and especially is not more than 150° C. The reaction is continued to give the desired extent of reaction and especially is effected for a time of at least one hour, particularly at least two hours and especially at least four hours. A reaction time of more than 20 hours is generally not required and particularly the reaction time is not more than 15 hours and especially not more than ten hours. As will be appreciated, the reaction time and temperature are related, a shorter required time being required at higher reaction temperatures. The reaction is preferably effected in solution in a suitable solvent such as glacial acetic acid, cellosolve and high boiling alcohols.

The Schiff's base which is formed initially may be hydrolysed using an aqueous acid, for example sulphuric acid. The aqueous acid may be relatively concentrated, for example between 6N and 12N. The hydrolysis is effected at an elevated temperature which is typically at least 50° C. The temperature of hydrolysis generally does not exceed 100° C. The time of the hydrolysis should be sufficient to give a substantial extent of reaction to form the desired tetra-aldehyde. Preferably the reaction time is at least 30 minutes and especially at least one hour. In general a reaction time of more than 10 hours is not required. The reaction product can be obtained by cooling the reaction mixture, filtering and washing the reaction product.

The reaction product may be converted into the tetraoxime without being subjected to any additional purification beyond that achieved by filtration and washing. However, the reaction product may be purified further using any suitable method of purification. We have obtained a product of increased purity by eluting the product through a packed silica column using chloroform as the eluting liquid.

An aldehyde derivative may be obtained from a bis-phenol of formula (III) by the reaction of the phenol with formaldehyde and an arylamine followed by oxidation and hydrolysis, such a process being described in more detail in British patent specification 1563206.

A ketone derivative may be obtained from a bis-phenol of formula (III) by acylation of the phenol group, followed by rearrangement to give one ketone group in each ring and the repeating this process of acylation and rearrangement.

Compounds of the general formula (II) in accordance with the further aspect of the present invention include, inter alia, the tetra-aldehydes:
bis(4-hydroxy-3,5-diformylphenyl)methane,
2,2-bis(4-hydroxy-3,5-diformylphenyl)propane;
3,3-bis(4-hydroxy-3,5-diformylphenyl)pentane;
2,2-bis(4-hydroxy-3,5-diformylphenyl)pentane; and
1-phenyl-1,1-bis(4-hydroxy-3,5-diformylphenyl)ethane.

We have found that the compounds of the present invention are useful in providing surface protection properties.

Thus, in accordance with a further aspect of the present invention there is provided a process which comprises contacting at least part of a surface of a metal with a compound as hereinbefore defined.

The compound is a compound of the general formula (I) or (II) and is particularly a tetraoxime, for example a tetra-aldoxime.

The process of this further aspect of the present invention is especially suitable for the corrosion inhibition of iron, zinc, copper, tin and aluminium and in particular mild steel and the zinc surface of a galvanised steel.

The metal is contacted with the compound by treating the metal directly with the compound, particularly the tetraoxime, although it is generally preferred to apply the compound to the metal surface in the form of a solution in a suitable solvent. The tetraoxime is useful when used to provide a protective coating in its own right. However, the compound may be used as a metal pre-treatment before the application of a surface coating; or may be incorporated into a surface coating composition.

Conventional organic solvents may be used to dissolve the compounds, particularly the tetraoximes and these include for example alcohols, ethers, ketones and aliphatic and aromatic hydrocarbons. Especially preferred solvents are those having good wetting and drying properties and include for example ethanol, propano-2-ol, toluene, xylene, chloroform and 1,1,1-trichloroethane. A mixture of organic solvent with water may be used, for example when the organic solvent is a $C_1$–$C_6$ lower alcohol such as ethanol, propanol or propan-2-ol. The compounds of the present invention are essentially insoluble in water and hence if water is used as the liquid medium the compounds are used as a dispersion in the water.

The compounds of the present invention are typically solids and are preferably contacted with at least part of a surface of a metal as a solution or dispersion in a suitable liquid medium.

Thus, as a yet further aspect of the present invention there is provided a composition which comprises
a) a liquid solvent or dispersant or a surface coating composition and
b) a compound as hereinbefore defined.

Component a) may be a liquid in which component b) is dissolved or dispersed. Suitable liquids include aliphatic, cycloaliphatic and aromatic hydrocarbons, halogenated hydrocarbons, alcohols, esters and ketones, many of the compounds which are component b) being soluble in such liquids. Alternatively, the liquid can be water in which the compounds which are component b) are generally insoluble and hence, when component a) is water, the composition is generally a dispersion of component b) in water. Alternatively, the liquid may be a mixture such as an aqueous alcohol. If a liquid dispersant is used, this may include a suitable surfactant to aid dispersion of component b) in the liquid. Component a) may be a lubricating material, for example liquid paraffin or a synthetic polyalkylene glycol lubricant.

Alternatively, component a) is a surface coating composition, for example a film forming binder system. The film forming binder system which can be used as component (a) of the coating composition may be a paint (primer), a lacquer; a resin or other protective coating. Thus, component (a) may be solvent-based surface coating composition, for example a cellulose/solvent based primer paint such as those used for car "touch-up" paints. The compound which is component (b) of the coating composition is generally soluble to at least some extent in the solvents used for such primers and typically is added as a solid when being incorporated into such a primer paint system. Alternatively, component (a) may be an aqueous emulsion surface coating system, for example a primer or protective coating based on polymer latices such as for example acrylic and styrene/acrylic latices and vinyl acrylic co-polymer latices including acrylate modified vinyl chloridevinylidene chloride copolymer latices, and the compound which is component (b) may be used as a dispersion or suspension in such aqueous systems. The surface coating composition may be an alkali-removable protective coating composition of the addition polymer type in which the polymer contains carboxyl groups.

The film forming binder system which may be used as component (a) of the composition preferably contains an organic polymer and in general any such polymer used in the paint industry may be included in the composition. Thus, the suitable film forming binders include, for example, an alkyd resin, an epoxy resin, an oleoresin, a latex rubber, a chlorinated rubber, a vinyl resin such as polyvinylacetate or polyvinyl butyral, a polyurethane, a polyester, an organic or inorganic silicate, a polyamide or an acrylic polymer. It will be appreciated that the composition can include two or more compatible film forming polymers. The composition may also include an extender or plasticising resin, such as a hydrocarbon resin, or a coal tar derivative.

The film forming binder system which may be used as component (a) of the coating composition of the present invention can include homopolymers and copolymers of the following:
vinyl chloride
vinylidene chloride,
vinyl esters of alkanoic acids having from 1 to 18 carbon atoms in the alkyl group, especially vinyl acetate,
alkyl acrylates and methacrylates having from 1 to 18 carbon atoms in the alkyl group,
acrylamide and substituted acrylamides,
acrylonitrile, and methacrylonitrile,
monoethylenically unsaturated hydrocarbons, for example ethylene, isobutene, styrene and alpha-methyl styrene.

Example of polymers usable when component (a) is a film forming binder system are "acrylic polymers", by which is meant those polymers comprising predominantly units of alkyl acrylates and/or methacrylates having from 1 to 12 carbon atoms in the alkyl group, sometimes containing an acid functionally by virtue of containing polymerised units of one or more aliphatic unsaturated alpha-beta unsaturated carboxylic acids. Polymers of this type are described in European Patent Application No. 0115694.

Other examples of polymers usable when component (a) is a film forming binder system are copolymers of (i) vinyl chloride, (ii) vinylidene chloride and (iii) one or more alkyl acrylates or alkyl methacrylates having from 1 to 12 carbon atoms in the alkyl group; such polymers may optionally also contain polymerised units of one or more aliphatic alpha-beta unsaturated carboxylic acids. Copolymers of this type are described generally and specifically in the specification of UK Patent No. 1558411.

Alkyd containing resins are extensively used as the film forming binder in paint systems and the composition may be one in which component (a) is a film forming system which is, or contains, an alkyd containing resin, particularly an oil-modified alkyd.

The polymer or polymers which is, or are, used when component (a) is a film forming binder system, is usually used in an amount of from 5 to 60% (based on weight in grams of the polymers per 100 cm$^3$ of the composition), and more usually 10 to 40%. The polymer may be dissolved or colloidally dispersed (that is exist as an emulsion, with an average particle size usually below two micrometres) in a suitable liquid carrier medium.

Component (a) may be any material which can be contacted with a surface either to provide a coating thereon or to provide lubrication. Thus, component (a) may be a natural oil or grease which has been derived from animals or plants, such as, for example, lanolin or rape seed oil. Alternatively, component (a) may be a petroleum refined product such as a lubricating oil, turbine oil, fuel oil, gasoil or grease, which are used in circumstances in which they contact if only temporarily, a metal surface.

Component (b) of the composition of the present invention is preferably a tetraoxime as hereinbefore defined.

The compositions of the present invention can be contacted with at least part of a surface of a metal and we have found that the coated surface has an increased resistance to corrosion. The compositions are suitable for the corrosion inhibition of iron, zinc, copper, tin and aluminium, particularly mild steel and the zinc surface of galvanised steel.

The use of the composition of the present invention to provide a corrosion inhibiting coating may be combined with a conventional corrosion inhibition treatment such as, for example, the phosphating of iron. Furthermore, the composition may include, in addition to the compound which is component (b), other materials, particularly those which have been proposed as corrosion inhibitors. Thus, the composition may include a metal oxide or as an alternative to, or in addition to, the metal oxide, the composition may also include a metal phosphate, particularly a phosphate of the metal which is present in the metal oxide.

Thus, as a further aspect of the present invention the composition may also include at least one of a metal oxide and a metal phosphate.

The composition of the present invention may be a lubricant composition in which component (a) is a lubricating oil or a grease. We have found that such compositions give resistance to corrosion and/or improved anti-wear characteristics when used in contact with moving metal surfaces.

The composition of the present invention typically contains from 0.1 to 30% by weight of the compound relative to the total volume of the composition and preferably the compound is present in an amount of 0.1 to 5% w/w. If component (a) of the composition is an emulsion of a film forming binder system in a liquid medium, the compound which is component (b) may give a useful effect when dispersed in the emulsion in an amount of from 0.1 to 15% w/w. If the composition is a lubricant composition the compound is typically present in such a composition in an amount of from 0.1 up to 10% wt/wt, preferably from 0.5 to 6% wt/wt.

In addition to the compound of the present invention and the liquid solvent or dispersant or the surface coating composition, the composition of the present invention may include various other ingredients such as those commonly employed in the film forming coating compositions such as defoamers, rheology control agents, thickeners, dispersing and stabilising agents (usually surfactants), wetting agents, extenders, fungicides, pigments or colorants of one sort or another, coalescing solvents, plasticisers, and anti-freeze agents. Furthermore, as noted previously herein, the composition may also include one or more known corrosion inhibitors.

The composition of the present invention may be prepared using any one of the techniques which have been used for incorporating solids into a liquid or plastic medium in which the solid is essentially insoluble. Thus, if component (a) is a film forming coating composition, techniques for preparing paint compositions may be used, for example by mixing components either in a grinding apparatus or pre-mixing the components and then grinding. The compound of the present invention and any optional metal oxide, metal phosphate or other corrosion inhibitor, may be incorporated into the surface coating composition at any convenient stage, for example during the grinding together of the components of the paint formulation.

As noted previously herein, the composition of the present invention may be coated onto a metal to provide a corrosion inhibiting coating on the metal.

Thus, as a further aspect of the present invention there is provided a process which comprises contacting, for example by coating, at least part of a surface of a metal with a composition as hereinbefore defined.

The process of the present invention results in a coated surface which typically has an increased resistance to corrosion and is especially suitable for the corrosion inhibition or iron, zinc, copper, tin and aluminium, particularly mild steel and the zinc surface of a galvanised steel.

The composition may be applied to the metal surface in conventional manner, for example by dipping, spraying or brushing. The temperature of the application may be any suitable temperature for example from 0° to 50° C.

The metal surface which is coated with the composition may be brightly polished and/or freshly cleaned, but a lightly rusted surface may be coated by the process of the present invention. Thus the composition may be coated onto a surface in an "as received" condition, and it may be unnecessary for the surface to be freshly cleaned or brightly polished.

The process of the present invention provides a corrosion inhibiting coating on the surface of a metal and may be combined with conventional corrosion inhibition treatments such as the phophating of iron.

The process of the present invention may be used to provide corrosion inhibition as a pre-treatment before application of a known surface coating. Thus the coating step may be used, for example, to provide temporary protection whilst the metal is being transferred from one sit to another. Hence the process of the present invention may be used for the temporary protection of a metal surface and the protective coating subsequently removed before or during further processing.

A further feature of the present invention is a metal surface treated with the compound of Formula I having an improved resistance to corrosion.

Thus, as a yet further feature of the present invention there is provided a metal article, at least part of one surface of which has a coating which is a tetraoxime as hereinbefore defined or which is a composition as hereinbefore described and which contains a tetraoxime as hereinbefore defined.

The surface of the metal is preferably coated with a composition which contains the tetraoxime and a known corrosion inhibitor.

As a yet further aspect of the present invention the composition is a lubricant composition in contact with metal surfaces which are in relative motion. The lubricant composition provides improved resistance to corrosion and/or anti-wear characteristics in such a system.

Various aspects of the present invention are set out in more detail hereafter in the following illustrative examples in which all parts and percentages are by weight unless other wise stated.

EXAMPLE 1 a) Preparation of 2,2-bis(4-hydroxy-3,5-diformylphenyl)propane

A mixture containing 2,2-bis(4-hydroxyphenyl)propane (55.6 parts by weight), hexamethylenetetraamine (136 parts by weight), glacial acetic acid (1000 parts by weight), and water (29 parts by weight) was stirred and heated to a temperature of between 120° and 125° C., at which temperature the mixture boiled. Stirring of the boiling mixture was continued under conditions of reflux for 7 hours. The source of heat was then removed and the reaction mixture was stirred whilst cooling to ambient temperature overnight. A pale yellow solution was obtained which was warmed to 80°±2° C. A solution containing water (500 parts by weight) and concentrated (98%) sulphuric acid (180 parts by weight) was added all at once. Stirring and heating at 80°±2° C. was continued for 3 hours, then the reaction solution was cooled to 25° C. by immersion of the reaction vessel in water at 10° C. to 15° C.

The cooled reaction mixture was poured into a mixture of ice and water (4000 parts by weight) which was being stirred and a suspension was formed which was stirred for one hour at a temperature between 5° and 10° C. The suspended solid was isolated by filtration, washed with three portions (each of 1000 parts by weight) of cool (10° C.) water, and dried at 25° C. in vacuo (20–25 Torr) for 24 hours. 49.7 parts by weight (60% yield based on the starting phenol) of a pale yellow solid was obtained. This solid contained the tetraaldehyde (2,2-bis(4-hydroxy-3,5-diformylphenyl)propane).

b) Purification of aldehyde

The product of part (a) (10 parts by weight) was dissolved in chloroform (50 parts by weight). Silica type 62 (20 parts by weight, obtained from W. R. Grace and Co Ltd), was added to the solution. The mixture obtained was evaporated to dryness at 60° C. and a pressure of 20–25 Torr using a rotary evaporator. A solid was obtained which was added to the top of a glass column packed with silica Type 62 (500 parts by weight), and elution with chloroform was commenced. Appropriate fractions (as determined by comparative thin-layer chromatography) which were eluted from the base of the column were combined and evaporated to dryness, producing 3.85 parts of a very pale yellow crystalline solid having a melting point of 170°–173° C. By analysis this compound contained C,67.1% by wt and H,4.9% by wt; 2,2-bis(4-hydroxy-3,5-diformylphenyl)propane ($C_{19}H_{16}O_6O$ requires: C, 67.0% by wt and H,4.7% by wt. Proton n.m.r. of a solution in deuterated chloroform gave shifts (p.p.m.) of 1.80(s 6H, 2X $\underline{CH_3}$); 8.0 (s 4H, 4X aromatic $\underline{H}$); 10.3(s, 4H, 4X $\underline{CH}=O$).

High performance liquid chromatography confirmed the presence of only one component in this material.

EXAMPLE 2

An aqueous solution of hydroxylamine was prepared by stirring together a mixture of hydroxyammonium chloride (7.0 parts by weight), anhydrous sodium carbonate (5.5 parts by weight) and water (40 parts by weight) for ten minutes at between 20° and 25° C.

The solution of hydroxylamine was added all at once to a suspension which was being stirred and which contained the product of Example 1 part (a) (5.0 parts by weight) in industrial methylated spirits (100 parts by weight). External heating was then applied to raise the temperature of the mixture to between 70° and 80° C. Stirring and heating were maintained for four hours under these conditions. The product was isolated by pouring the reaction mixture into cold (10° C.) water (3000 parts by weight), stirring for ten minutes, filtering, washing the collected solid with water, and finally drying at 25° C. in vacuo (20–25 Torr) for 24 hours. The yield of product was 5.0 parts by weight of a solid having a melting point of 240°–50° C. By analysis the product was found to contain C,56.3% by weight; H,5.6% by weight; and N,11.6% by weight.

High performance liquid chromatography, in conjunction with mass spectral measurements, confirmed that the major component in this material was 2,2-bis(4-hydroxy-3,5-dioximinomethylphenyl)propane [M+400].

EXAMPLE 3

An aqueous solution of hydroxylamine was prepared by stirring together a mixture containing hydroxyammonium chloride (2.7 parts by weight), anhydrous sodium carbonate (2.0 parts by weight) and water (30 parts by weight). After 10 minutes stirring at between 20° and 25° C., a clear solution was obtained. The solution was added all at once to a suspension which was being stirred and contained the product of Example 1 part (b) (2.0 parts by weight) in A.R. grade methanol (250 parts by weight). The reaction mixture was heated to between 55° and 60° C. and stirred at this temperature for one hour, then poured into a beaker containing cold water at below 10° C. (3000 parts by weight) which was being stirred. After stirring for ten minutes, the solid which had been precipitated was isolated by filtration, washed with cold water, and dried in vacuo (20–25 Torr) at 25° C. for 24 hours. The yield of product was 1.25 parts by weight of a white crystalline solid having a melting point of 250°–3° C. By analysis the product was found to contain, C,54.5% by weight; H,5.2% by weight; and N,12.8% by weight. The compound 2,2-bis(4-hydroxy-3,5-dioximinomethylphenyl)propane ($C_{19}H_{20}O_6N_4H_2O$) requires: C54.5% by weight; H,5.3% by weight; and N, 13.4% by weight. Mass spectral measurements (M+400) were consistent with the product being 2,2-bis(4-hydroxy-3,5-dioximinomethylphenyl)propane. Proton n.m.r. of a solution in a mixture of deuterated chloroform and deuterated dimethylsulphoxide gave shifts (ppm) of: 1.70 (s,6H,2X-CH$_3$); 7.55(s,4H,4X aromatic H); 8.45(s,4H, 4X-CH=N); 11.0(s,2H,exchange with D$_2$O,2X aromatic-OH); 11.6(s, 4H, exchange with D$_2$O, 4X N-OH).

EXAMPLE 4

The product of Example 2 (0.5 parts by weight) was dissolved in propan-2-ol (60 parts by weight) with stirring at 25° C. Distilled water was then added in an amount to give 100 parts in total and to produce a clear solution. Samples of zinc-coated steel, obtained from British Steel and labelled MINIMUM SPANGLE GALVATITE were cut into coupons measuring 4 inches by 1 inch (10.16 cm×2.54 cm). These coupons were cleaned by successive immersion in a) boiling 1,1,1-trichloroethane for five minutes; b) the vapour above boiling 1,1,1-trichloroethane for 20 seconds; c) an aqueous solution of 15gdm$^{-3}$ of RIDOLENE 1089 (a proprietary alkaline detergent for cleaning metal surfaces) for ten seconds at 60° C.; d) cold running tap water; e) cold distilled water. The coupons were then dried in a current of warm air for 30 seconds.

Three coupons cleaned in the manner described were immersed in the solution prepared as described herein and containing the product of Example 2. Immersion was for a time of five minutes at 25° C., and the coupons were then removed, allowed to drain for 30 seconds, then dried in a current of warm air. The edges of each coupon were coated with a protective film of butyl rubber which was allowed to dry.

Each coupon was then immersed in distilled water contained in a separate glass jar, and allowed to stand at a temperature of between 20° and 25° C.

Negative control coupons were prepared by immersing cleaned panels in a mixture of propan-2-ol and water (50 parts by weight of each component) for 5 minutes at 25° C., then proceeding exactly as described above for the coupons treated with the solution containing the product of Example 2.

The distilled water in each glass jar was replaced with fresh liquid at approximately 48 hour intervals. The extent of corrosion of each test coupon was recorded as an estimate of the area of metal which had corroded to produce encrustations of white or grey corrosion products.

None of the coupons treated with the solution containing the product of example 2 showed any evidence of corrosion after 100 hours' immersion in the distilled water. After 264 hours, approximately 40% of the surface of the coupons were corroded. The surface of the coupons became totally covered in corrosion products after 650 hours. The control coupons, however, were completely encrusted in grey corrosion products within 24 hours.

EXAMPLE 5

The product of Example 2 (0.02 parts by weight) was dissolved in a mixture of isopropanol (9 parts) and water (1 part). This solution was metered onto the zinc surface (coupons cleaned as in Example 4) by the use of a drawing bar (K-bar), designed to produce a wet film thickness of 24 microns, and hence an approximate dry coating weight of 50 mgm$^{-2}$ of the product. These coupons were dried in warm air and subjected to corrosion tests in exactly the same manner as described herein.

After immersion in distilled water for 650 hours, complete surface corrosion was evident on coupons treated with the solution of the product of Example 2. Negative control coupons, coated only with a mixture of propan-2-ol and water had suffered complete surface corrosion within 24 hours of being immersed in distilled water.

EXAMPLE 6

In an exactly analogous manner to that described in Example 4, cleaned zinc-steel coupons were treated with a solution of the product of Example 3 (0.5 parts by weight).

Subsequent corrosion tests, performed exactly as described in Example 4 showed that surface of coupons treated with the product of Example 3 had not corroded after immersion in distilled water for 200 hours and the surface was not fully corroded until 650 hours had elapsed.

EXAMPLE 7

The procedure described in Example 5 was used to meter a solution of the product of Example 3 (0.2% by wt) onto zinc-steel coupons. Subsequent corrosion tests performed as described in Example 4 showed that coupons treated with a solution of the product of Example 3 had developed extensive surface corrosion after immersion in distilled water for 650 hours.

EXAMPLE 8

3,3-bis(4-hydroxy-3-dioximinomethylphenyl)pentane, and the intermediate tetra-aldehyde product were prepared from 3,3-bis(4-hydroxyphenyl)pentane using the procedure as described in Example 1, part (a) and Example 2. Yield of the tetraoxime product was 74.9% of a solid having a melting point in the range 167°–172° C. This product was found by elemental analysis to contain: C, 57.6% by weight; H, 6.1% by weight; and N, 11.0% by weight: 3,3-bis(4-hydroxy-3-dioximinomethylphenyl)pentane (C$_{21}$H$_{24}$O$_6$N$_4$ 0.53H$_2$O) requires: C, 57.6% by weight; H, 5.7% by wt; N, 12.8% by wt.

Proton n.m.r. was consistent with the product being the tetraoxime phenyl pentane derivative.

EXAMPLE 9

The product of Example 8 (0.02 parts by weight) was dissolved in propan-2-ol (9 parts) and water (1 part) by the method used in Example 4. Cleaned zinc-steel coupons (as in Example 4) were coated with the solution, dried, and the corrosion resistance determined using the method described in Example 4. Coupons treated with the solution of the product of Example 8 had not developed any surface corrosion after 200 hours and did not become fully corroded on the surface until 650 hours had elapsed. Negative control coupons were extensively corroded after 24 hours.

EXAMPLES 10 AND 11

The products of Examples 2 and 3 were each dissolved (0.1 parts by weight) in isopropanol (20 parts by volume). The solutions obtained were applied to the surfaces of zinc coated steel coupons, cleaned as described in Example 4, by the process of Example 5 and were then dried in warm air and subjected to the corrosion test of Example 4.

By way of comparison further solutions were prepared using 2-hydroxy-5-nonylbenzaldoxime or 2,6-bis-(oximinomethyl)-4-nonylphenol (0.1 parts by weight) in isopropanol (20 parts by volume). The comparative solutions were applied to the surfaces of zinc coated steel coupons and subjected to a corrosion test in the same manner as the solutions of the products of Examples 2 and 3. The use of optionally substituted 2-hydroxy-5-alkylbenzaldoximes such as 2-hydroxy-5-nonylbenzaldoxime to inhibit corrosion is the subject of our Euorpean Patent No 125025 and the use of optionally substituted 2,6-bis(oximinomethyl)-4-alkylphenols such as 2,6-bis(oximinomethyl)-4-nonylphenol to inhibit corrosion is the subject of our European Patent No 178850.

The results obtained at various times are set out in Table One.

TABLE ONE

| Ex or Comp Ex | Inhibitor (a) | % surface corrosion after time (hours) | | | | |
|---|---|---|---|---|---|---|
| | | 24 | 160 | 350 | 664 | 856 |
| 10 | 2 | 0 | 7 | 15 | 95 | 100 |
| 11 | 3 | 0 | 17 | 27 | 75 | 85 |
| A | HNBO | 0 | 100 | — | — | — |
| B | BOMNP | 0 | 55 | 100 | — | — |
| C | NIL | 100 | — | — | — | — |

Notes to Table One
(a) 2 is the product of Example 2
3 is the product of Example 3
HNBO is 2-hydroxy-5-nonylbenzaldoxime
BOMNP is 2,6-bis(oximinomethyl)-4-nonylphenol.

EXAMPLES 12 AND 13

Aluminium clad aluminium alloy coupons (4"×1"×0.063"; 2024 T3) were degreased by suspending in the vapour of 1,1,1-trichloroethane. The coupon was then agiated in a solution of 0.1% weight/volume tetraoxime in ethanol at 50° C. for 3 hrs. The coupon was then removed, rinsed in ethanol and dried.

Corrosion inhibition was determined by immersing the treated aluminium coupon in de-ionised water at 20°-25° C. and inspecting the coupons periodically for appearance of a black 'tarnish' on the surface of the coupon.

The results obtained are given in Table Two.

TABLE TWO

| Ex or Comp Ex | Inhibitor (b) | Time taken to tarnish (days) (c) |
|---|---|---|
| 12 | 2 | GT 66 |
| 13 | 8 | GT 66 |
| 14 | 1 | 28 |
| Control | Nil | 18 |

Notes to Table Two
(b) 2, 8 and 1 are the products of Examples 2, 8 and 1
(c) GT is greater than.

I claim:
1. A compound of the general formula

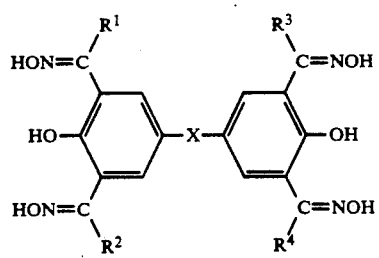

wherein
$R^1$, $R^2$, $R^3$ and $R^4$ are each, independently, hydrogen, a $C_{1-20}$-hydrocarbon group or a $C_{1-20}$-hydrocarbon group substituted by hydrocarbonoxy, halogen, nitro or nitrile; and
X is a direct bond or a divalent linking group.

2. A compound as claimed in claim 1 wherein $R^1$, $R^2$, $R^3$ and $R^4$ are all hydrogen.

3. A compound as claimed in claim 1 wherein the group X is selected from the group consisting of methylene, ethylene, ethylidene, propylene, propylidene, dimethylmethylene, butylene, pentylene, phenylmethylene, and methylphenylmethylene.

4. A compound selected from the group consisting of bis(4-hydroxy-3,5-dioximinomethylphenyl)methane;
2,2-bis(4-hydroxy-3,5-dioximinomethylphenyl)propane;
3,3-bis(4-hydroxy-3,5-dioximinomethylphenyl)pentane;
2,2-bis(4-hydroxy-3,5-dioximinomethylphenyl)pentane; and
1-phenyl-1,1-bis(4-hydroxy-3,5-dioximinomethylphenyl)ethane.

5. A process which comprises contacting at least part of a surface of a metal with a compound as claimed in claim 1.

6. A process as claimed in claim 5 wherein the metal is iron, zinc, copper, tin or aluminium.

7. A composition which comprises
a) a liquid solvent or dispersant or a surface coating composition; and
b) a compound as claimed in claim 1.

8. A metal article which has been coated on at least part of one surface thereof by a compound as claimed in claim 1.

* * * * *